US00PP09758P

United States Patent [19]

Sapia

[11] Patent Number: Plant 9,758

[45] Date of Patent: Dec. 24, 1996

[54] CARNATION PLANT NAMED 'VELVET'

[75] Inventor: Flavio Sapia, San Remo, Italy

[73] Assignee: Messick Company, Saratoga, Calif.

[21] Appl. No.: 517,106

[22] Filed: Aug. 21, 1995

[51] Int. Cl.[6] ..... A01H 5/00

[52] U.S. Cl. ..... Plt./70.7

[58] Field of Search ..... Plt./70.7

*Primary Examiner*—James R. Feyrer

*Attorney, Agent, or Firm*—Proprietary Rights International

[57] ABSTRACT

A distinct cultivar of Carnation plant named Velvet, characterized by its purple petal color; compact growth habit; freely branching habit; and proportional plant size.

1 Drawing Sheet

The present invention relates to a new and distinctive cultivar of Carnation plant, botanically known as *Dianthus caryophyllus*, and hereinafter referred to by the cultivar name Velvet.

The new cultivar is a product of a planned breeding program conducted by the inventor in San Remo, Italy. The objective of the breeding program was to create new potted Carnation cultivars having different or more vivid flower colors.

The new cultivar originated from a cross made by the inventor of the proprietary selection of the breeder designated as V-123, as the male or pollen parent with the proprietary selection of the breeder designated as V-41, as the female or seed parent.

The cultivar Velvet was discovered and selected by the inventor as a flowering plant within the progeny of the stated cross in a controlled environment in San Remo, Italy. Asexual reproduction of the new cultivar by terminal cuttings taken at San Remo, Italy, has shown that the unique features of this new Carnation are stabilized and reproduced true to type in successive generations.

The culivar Velvet has not been observed under all possible environmental conditions. The phenotype may vary somewhat with variations in environment such as temperature, daylength, and light intensity, without, however, any variance in genotype. The following observations, measurements and comparisons describe plants grown in Palisade, Colo. under commercial practice in a polyethylene-covered greenhouse.

The following traits have been repeatedly observed and are determined to be the unique characteristics of Velvet. These characteristics in combination distinguish Velvet as a new and distinct cultivar:

1. Purple petal color.
2. Compact growth habit.
3. Freely branching habit.
4. Proportional flowers to foliage ratio.

Compared to its parent, proprietary selection V-123, the new Carnation is more compact and flower color is purple compared to the pink with crimson eye flower color of selection V-123. Compared to its parent, proprietary selection V-41, the new Carnation is more compact, more freely branching and bushier, has longer and broader leaves, shorter stem internodes, and flower color is purple compared to the pink flower color of selection V-41.

The accompanying colored photograph illustrates the overall appearance of the new cultivar, showing the colors as true as it is reasonably possible to obtain in colored reproductions of this type. The flower color appears more red than the actual flower color due to light reflectance. The photograph comprises a top perspective view of a flowering stem, flower, petals, flower bud and reproductive organs from a typical potted plant of Velvet grown in a polyethylene-covered greenhouse in Palisade, Colo.

In the following description, color references are made to The Royal Horticultural Society Colour Chart except where general terms of ordinary dictionary significance are used. Measurements and numerical values represent averages for at least three typical plants grown in 10-cm containers with day temperatures of 24 C., night temperatures of 18 C., and a light level of 4,500 foot-candles.

Botanical classification: *Dianthus caryophyllus* cultivar Velvet.

Parentage:

*Male.*—V-123, a proprietary selection of the breeder.

*Female.*—V-41, a proprietary selection of the breeder.

Propagation:

*Type cutting.*—Terminal cuttings.

*Time to initiate roots.*—20 days at 21° C. soil temperature.

*Rooting habit.*—Numerous, fibrous, and well-branched.

Plant description:

*Form.*—Compact flowering potted plant.

*Habit of growth.*—Freely branching, bushy and dense.

*Plant height at flowering.*—Compact, 15 to 17 cm.

*Vigor.*—Moderate to high vigor.

*Foliage description.*—Leaves simple, opposite, generally symmetrical, abundant. Size: Length: 3 to 5 cm. Width: 8 mm. Shape: Narrow, lanceolate with acute leaf tip. Texture: Leathery, glabrous. Margin: Entire. Color: Young foliage top side: 143D. Young foliage under side: 143A. Mature foliage top side: 147A. Mature foliage underside: 147A. Stem color: 141A. Venation: Prominent mid-vein.

Flower description:

*Flower type and habit.*—Semi-double flowers that are slightly cupped with an open center. Freely and continuously flowering.

*Inflorescences borne.*—Clusters of 5 to 7 flowers on strong peduncles borne above foliage, arising from terminal shoot and leaf axils. Flowers persistent and slightly fragrant.

*Flower longevity.*—14 days on the plant.

*Flower diameter.*—3.8 to 4 cm.

*Flower depth.*—2 cm.

*Flower buds.*—Shape: Cylindrical. Size: Length: 1.5 to 1.8 cm. Width (diameter): 6 to 8 mm. Opening rate: 4 to 5 days.

*Petals.*—Quantity: 10 to 14. Shape: Fan-shaped. Tip: Dentate, deeply serrated. Size: Length: 1.3 cm. Width: 1.5 cm. Color: Velvety appearance. Outer edge, immature: Deep magenta, 71B. Center band, immature: Darker magenta, 71A. Outer edge, mature: Deep magenta, 71B. Center band, mature: Darker magenta, 71A. Under side, mature: 58A. Fade: Petal color does not fade or discolor.

*Calyx.*—Shape: Cylindrical. Splitting: Not observed. Sepal quantity: 5. Sepal shape: Ovate. Sepal tip: Acute. Sepal size: Length: 1 cm. Width: 5 mm. Sepal color: Outside: 141B. Inside: 141C.

*Peduncle.*—Character: Stiff and upright. Color: 141A.

*Reproductive organs.*—Stamens: Arranged evenly around ovary. Stamen number: 8. Filament: 1 to 1.1 cm, very fine diameter. Anthers: White. Pollen: White. Pistils: Style length: 1.6 to 1.8 cm. Stigma color: Pink. Ovaries: 2.

Disease resistance: No known Carnation diseases observed to date.

Seed production: Self-fertile. Fruit is lozenge-shape and yellowish brown at maturity.

It is claimed:

1. A new and distinct cultivar of Carnation plant named Velvet, as illustrated and described.

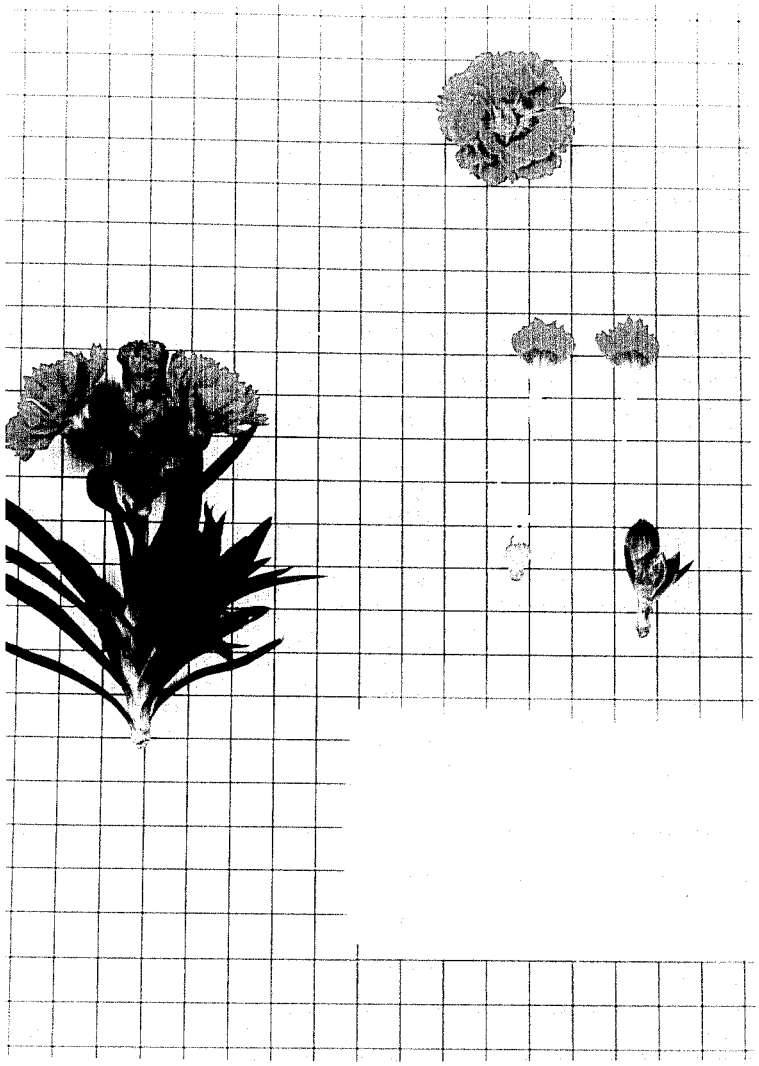

* * * * *